United States Patent [19]

Rosenkrantz et al.

[11] 4,327,087

[45] Apr. 27, 1982

[54] STABILIZED NETILMICIN FORMULATIONS

[75] Inventors: Bernard E. Rosenkrantz, Bloomfield; Elliot Stupak, West Caldwell, both of N.J.

[73] Assignee: Schering Corporation, Kenilworth, N.J.

[21] Appl. No.: 141,029

[22] Filed: Apr. 17, 1980

Related U.S. Application Data

[63] Continuation-in-part of Ser. No. 869,741, Jan. 16, 1978, Pat. No. 4,223,022.

[51] Int. Cl.³ .................... A61K 31/71; C07H 15/22
[52] U.S. Cl. .................................. 424/180; 424/181; 536/17 R
[58] Field of Search .............. 424/180, 181; 536/17 R

[56] References Cited

U.S. PATENT DOCUMENTS

| | | | |
|---|---|---|---|
| 3,962,429 | 6/1976 | Furuno et al. | 424/181 |
| 4,000,262 | 12/1976 | Daniels et al. | 536/17 R |
| 4,009,328 | 2/1977 | Mallams et al. | 536/17 R |
| 4,044,123 | 8/1977 | Daniels et al. | 536/17 R |
| 4,107,435 | 8/1978 | Ross | 536/17 R |
| 4,212,860 | 7/1980 | McCombie | 536/17 R |
| 4,223,022 | 9/1980 | Rosenkrantz et al. | 536/17 R |

Primary Examiner—Johnnie R. Brown
Attorney, Agent, or Firm—Vincent H. Gifford; Warrick E. Lee, Jr.; Bruce M. Eisen

[57] ABSTRACT

A highly pH- and color-stabilized parenteral formulation is provided comprising an aqueous solution of a salt of an aminoglycoside containing an allylic amine and having a pH between 5.0–7.0.

6 Claims, No Drawings

STABILIZED NETILMICIN FORMULATIONS

This is a continuation-in-part of application Ser. No. 869,741, filed on Jan. 16, 1978, now U.S. Pat. No. 4,223,022.

Aminoglycosides have long been recognized as effective antibacterial agents. Interest within this series has recently focused on a potent subclass which is characterized by the presence of a pyranose ring which is unsaturated between the 4' and 5' positions and wherein the 5' position bears an amino alkyl substituent. Such aminoglycosides will be referred to hereinafter as those containing allylic amines. Examples of known antibiotics of this class are sisomicin (U.S. Pat. No. 3,832,286); netilmicin (U.S. Pat. No. 4,002,742); verdamicin (U.S. Pat. No. 3,988,316); Antibiotic G-52 (U.S. Pat. No. 3,956,068); Antibiotic 66-40B (U.S. Pat. No. 3,880,828); and Mu-1, Mu-2, Mu-4, Mu-5 and Mu-6, (U.S. Pat. No. 4,011,390). Mu-6 (5-epi-sisomicin) has the USAN recognized name of Pentisomicin. These antibiotics are generally administered in the form of a parenterally acceptable acid addition salt, e.g. sisomicin sulfate. For purposes of this specification, the term "antibiotic" will include synthetic derivatives.

Unfortunately, these allylic amine-containing aminoglycosides are highly prone to oxidative decomposition when exposed to the air for even relatively short periods of time, particularly at elevated temperatures. This oxidative decomposition results in the rapid formation of colored impurities (chromophoric material), eventually resulting in a loss of potency and pharmaceutical elegance, along with the production of materials of unknown toxicology. For this reason the compositions are generally packaged in an oxygen free environment, e.g., under nitrogen. The only aminoglycoside of this subclass which as been marketed, sisomicin sulfate, has an initial pH of less than 4.0 and a comparatively short shelf life. It would be highly desirable to significantly increase the shelf life of such antibiotic systems. For purposes of this specification, "shelf life" refers to the length of time in which the color of the formulation is below 1200 APHA color units and the pH is above 2.5. An APHA color unit is a widely recognized standard described, for example, in *Standard Method for the Examination of Water and Waste Water,* 13th Edition, 1971, American Public Health Association.

We have now surprisingly found that a highly pH-and color-stable parenteral aqueous solution of the subject unsaturated aminoglycoside is obtainable if the initial pH of the system is within the range of 5.0-7.0. A more preferred pH range is 5.8-6.8, with the most preferred pH range being 6.2-6.5. The resultant shelf life significantly exceeds that of the aforementioned prior art formulation having an initial pH of less than 5.0, or a formulation having a pH greater than 7.0. In the preferred pH range of 5.8-6.8, the pH is found to be particularly stable and the product thereby has more predictable characteristics. In the most preferred pH range of 6.2-6.5, the product is found to have a particularly stable pH even in the presence of oxygen, e.g., air.

This result is unexpected since one would not have anticipated that both color-and pH-stability would be greatly improved for the subject formulations by selection of such a narrow initial pH range. Aminoglycosides have classically been marketed with initial pH's in the range of about 3.5 to 4.5.

The desired pH range can be achieved by upward adjustment of the pH with a suitable base such as sodium hydroxide or downward adjustment with a suitable acid such as hydrochloric acid. In a preferred embodiment, the desired initial pH is established by appropriately selecting an antioxidant or combination of antioxidants which will give the desired pH without need for a discrete pH adjustment.

The preferred aminoglycoside compositions of this invention involve sisomicin sulfate in a concentration of 10-50 mg/ml of solution, netilmicin sulfate in a concentration of 10-100 mg/ml of solution and 5-epi-sisomicin in a concentration of 10-50 mg/ml of solution.

Antioxidants are generally required in the formulation, particularly at higher concentrations of the antibiotic. The preferred antioxidants are sodium metabisulfite, sodium bisulfite and sodium sulfite, or combinations thereof, with the choice of salt largely depending upon the initial pH of the system which is to be stabilized. These antioxidant agents act by being either preferentially oxidized (reducing agents), and thereby gradually used up, or by blocking an oxidative chain reaction. Other suitable antioxidants for an aqueous system are sodium thiosulfate, sodium formaldehyde sulfoxylate, acetone sodium metabisulfite, ascorbic acid, isoascorbic acid, thioglycerol, thiosorbitol, thioglycolic acid and cysteine hydrochloride.

Numerous other parenterally acceptable ingredients in their usual amount can be optionally added to the composition, such as preservatives, e.g. parabens, benzyl alcohol; electrolytes to make the solutions isotonic with body fluids, e.g. sodium chloride and sodium sulfate; and chelating agents, e.g. disodium EDTA.

The formulation of the aforesaid commercially available aqueous solution of sisomicin sulfate is shown below. These solutions have an initial pH of 3.7-3.9. The composition has a label-recommended shelf life of 18 months at 30° C. which is much less than the shelf life of the improved system, e.g. Example 1.

PRIOR ART

| Injectable Solution | Per 1.0 ml |
| --- | --- |
| Sisomicin (charged as sisomicin sulfate) | 50.0 mg |
| Sodium Metabisulfite | 3.0 mg |
| Sodium Chloride | 3.6 mg |
| Methylparaben | 0.8 mg |
| Propylparaben | 0.1 mg |
| Disodium Edetate | 0.1 mg |
| Distilled Water, q.s. add | 1.0 mg |

EXAMPLE 1

A composition is prepared by adjusting the pH of the above prior art formulation to 5.2 by the addition of a 0.1 N sodium hydroxide solution. The resultant formulation has a shelf life of at least 36 months at 30° C.

EXAMPLE 2

A pharmaceutical composition is preferred by blending together the following ingredients in the manner hereinafter indicated.

| Injectable Solution | Per 1.0 ml | Per 50 liters |
| --- | --- | --- |
| Sisomicin (charged as sisomicin sulfate) | 50.0 mg | 2500 gms. |
| Sodium sulfite | 0.8 mg | 40 gms. |
| Sodium metabisulfite | 2.4 mg | 120 gms. |

-continued

| Injectable Solution | Per 1.0 ml | Per 50 liters |
| --- | --- | --- |
| Propyl paraben | 0.1 mg | 5 gms. |
| Methyl paraben | 0.8 mg | 40 gms. |
| Disodium EDTA | 0.1 mg | 5 gms. |
| Sodium chloride | 3.9 mg | 195 gms. |
| Distilled water, q.s. | 1.0 ml | 50 liters |

Procedure: For a 50 Liter Batch

Charge approximately 35 liters of the distilled water to a suitable stainless steel jacketed vessel and heat to about 70° C. Charge the methylparaben and propylparaben to the heated water and dissolve with agitation. When the parabens are completely dissolved, cool the contents of the tank to 25° C.–30° C. Sparge the solution with nitrogen gas and keep covered with nitrogen during subsequent processing. Charge and dissolve the disodium EDTA, sodium chloride, sodium sulfite and sodium metabisulfite. Charge and dissolve the sisomicin sulfate. Bring the batch volume up to 50 liters with the distilled water and agitate until homogenous.

Under sterile conditions, filter the solution through a suitable bacteria retentive filter collecting the filtrate in a filling tank.

Fill the product aseptically into sterile pyrogen free multiple dose vials, ampoules or syringes and seal.

A composition prepared according to Example 2 has an initial pH of about 5.2 and a shelf life of at least 36 months at 30° C. This procedure yields a formulation in the desired pH range without need for a discrete pH adjustment step.

EXAMPLE 3

A pharmaceutical composition is prepared by blending together the following ingredients in a manner similar to Example 2.

| Injectable Solution | Per 1.0 ml |
| --- | --- |
| Sisomicin (charged as sisomicin sulfate) | 50.0 mg |
| Sodium sulfite | 3.9 mg |
| Propyl paraben | 0.1 mg |
| Methyl paraben | 0.8 mg |
| Disodium EDTA | 0.1 mg |
| Sodium sulfate | 6.4 mg |
| Distilled water, q.s. | 1.0 ml |

A composition prepared according to Example 3 has an initial pH of 6.1 and a shelf life of at least 36 months as 30° C.

EXAMPLE 4

A pharmaceutical composition is prepared by blending together the following ingredients in a manner similar to Example 2.

| Injectable Solution | Per 1.0 ml |
| --- | --- |
| Sisomicin (charged as sisomicin sulfate) | 10.0 mg |
| Sodium metabisulfite | 2.4 mg |
| Sodium sulfite | 0.8 mg |
| Methyl paraben | 1.3 mg |
| Disodium EDTA | 0.1 mg |
| Sodium chloride | 5.8 mg |
| Distilled water, q.s. | 1.0 ml |

A composition prepared according to Example 4 has an initial pH of 5.5 and a shelf life of at least 36 months at 30° C.

EXAMPLE 5

A pharmaceutical composition is prepared by blending together the following ingredients in a manner similar to Example 2.

| Injectable Solution | Per 1.0 ml |
| --- | --- |
| Netilmicin (charged as netilmicin sulfate) | 10.0 mg |
| Sodium sulfite | 4.0 mg |
| Methyl paraben | 1.3 mg |
| Propyl paraben | 0.2 mg |
| Sodium chloride | 5.4 mg |
| Distilled water, q.s. | 1.0 ml |

A composition prepared according to Example 5 has an initial pH of 6.8 and a shelf life of at least 36 months at 30° C.

EXAMPLE 6

A pharmaceutical composition is prepared by blending together the following ingredients in a manner similar to Example 2.

| Injectable Solution | Per 1.0 ml |
| --- | --- |
| Netilmicin (charged as netilmicin sulfate) | 10.0 mg |
| Sodium metabisulfite | 2.4 mg |
| Sodium sulfite | 0.8 mg |
| Sodium chloride | 6.1 mg |
| Distilled water, q.s. | 1.0 ml |

A composition prepared according to Example 6 has an initial pH of 5.5 and a shelf life of at least 36 months at 30° C.

EXAMPLE 7

A pharmaceutical composition is prepared by blending together the following ingredients in a manner similar to Example 2.

| Injectable Solution | Per 1.0 ml |
| --- | --- |
| Netilmicin (charged as netilmicin sulfate) | 10.0 mg |
| Sodium metabisulfite | 2.1 mg |
| Sodium sulfite | 1.2 mg |
| Sodium chloride | 6.1 mg |
| Distilled water, q.s. | 1.0 ml |

A composition prepared according to Example 7 has an initial pH of 5.8 and a shelf life of at least 36 months at 30° C.

EXAMPLE 8

A pharmaceutical composition is prepared by blending together the following ingredients in a manner similar to Example 2.

| Injectable Solution | Per 1.0 ml |
| --- | --- |
| Netilmicin (charged as netilmicin sulfate) | 10.0 mg |
| Sodium metabisulfite | 2.1 mg |
| Sodium sulfite | 1.2 mg |
| Sodium sulfate | 19.4 mg |
| Distilled water, q.s. | 1.0 ml |

A composition prepared according to Example 8 has an initial pH of 6.0 and a shelf life of at least 36 months at 30° C.

EXAMPLE 9

A pharmaceutical composition is prepared by blending together the following ingredients in a manner similar to Example 2.

| Injectable Solution | Per 1.0 ml |
|---|---|
| Netilmicin (charged as netilmicin sulfate) | 10.0 mg |
| Sodium metabisulfite | 2.4 mg |
| Sodium sulfite | 0.8 mg |
| Sodium sulfate | 19.4 mg |
| Distilled water, q.s. | 1.0 ml |

A composition prepared according to Example 9 has an initial pH of 5.8 and a shelf life of at least 36 months at 30° C.

EXAMPLE 10

A pharmaceutical composition is prepared by blending together the following ingredients in a manner similar to Example 2.

| Injectable Solution | Per 1.0 ml |
|---|---|
| Netilmicin (charged as netilmicin sulfate) | 25.0 mg |
| Sodium sulfite | 0.8 mg |
| Sodium metabisulfite | 2.4 mg |
| Methyl paraben | 1.3 mg |
| Propyl paraben | 0.2 mg |
| Sodium sulfate | 2.6 mg |
| Disodium EDTA | 0.1 mg |
| Distilled water, q.s. | 1.0 ml |

A composition prepared according to Example 10 has an initial pH of 5.4 and a shelf life of at least 36 months at 30° C.

EXAMPLE 11

A Pharmaceutical composition is prepared by blending together the following ingredients in a manner similar to Example 2.

| Injectable Solution | Per 1.0 ml |
|---|---|
| Netilmicin (charged as netilmicin sulfate) | 2.5 mg |
| Sodium sulfite | 1.2 mg |
| Sodium metabisulfite | 2.1 mg |
| Methyl paraben | 1.3 mg |
| Propyl paraben | 0.2 mg |
| Sodium sulfate | 2.6 mg |
| Disodium EDTA | 0.1 mg |
| Distilled water, q.s. | 1.0 ml |

A composition prepared according to Example 11 has an initial pH of 5.7 and a shelf life of at least 36 months at 30° C.

EXAMPLE 12

A pharmaceutical composition is prepared by blending together the following ingredients in a manner similar to Example 2.

| Injectable Solution | Per 1.0 ml |
|---|---|
| Netilmicin (charged as netilmicin sulfate) | 25.0 mg |
| Sodium sulfite | 1.2 mg |
| Sodium metabisulfite | 2.1 mg |
| Methyl paraben | 1.3 mg |
| Propyl paraben | 0.2 mg |
| Sodium chloride | 1.5 mg |
| Disodium EDTA | 0.1 mg |
| Distilled water, q.s. | 1.0 ml |

A composition prepared according to Example 12 has an initial pH of 5.6 and a shelf life of at least 36 months at 30° C.

EXAMPLE 13

A pharmaceutical composition is prepared by blending together the following ingredients in a manner similar to Example 2.

| Injectable Solution | Per 1.0 ml |
|---|---|
| Netilmicin (charged as netilmicin sulfate) | 25.0 mg |
| Sodium sulfite | 4.0 mg |
| Methyl paraben | 1.3 mg |
| Propyl paraben | 0.2 mg |
| Sodium chloride | 4.2 mg |
| Distilled water, q.s. | 1.0 ml |

A composition prepared according to Example 13 has an initial pH of 6.4 and a shelf life of at least 36 months at 30° C.

EXAMPLE 14

A pharmaceutical composition is prepared by blending together the following ingredients in a manner similar to Example 2.

| Injectable Solution | Per 1.0 ml |
|---|---|
| Netilmicin (charged as netilmicin sulfate) | 50.0 mg |
| Sodium sulfite | 4.0 mg |
| Methyl paraben | 1.3 mg |
| Propyl paraben | 0.2 mg |
| Sodium chloride | 2.5 mg |
| Distilled water, q.s. | 1.0 ml |

A composition prepared according to Example 14 has an initial pH of 6.2 and a shelf life of at least 36 months at 30° C.

EXAMPLE 15

A pharmaceutical composition is prepared by blending together the following ingredients in a manner similar to Example 2.

| Injectable Solution | Per 1.0 ml |
|---|---|
| Netilmicin (charged as netilmicin sulfate) | 100.0 mg |
| Sodium sulfite | 4.0 mg |
| Methyl paraben | 1.3 mg |
| Propyl paraben | 0.2 mg |
| Distilled water, q.s. | 1.0 ml |

A composition prepared according to Example 15 has an initial pH of 6.0 and a shelf life of at least 36 months at 30° C.

EXAMPLE 16

A pharmaceutical composition is prepared by blending together the following ingredients in the manner hereinafter indicated.

| Injectable Solution | Per 1.0 ml |
|---|---|
| 5-Episisomicin | 50.0 mg |

| Injectable Solution | Per 1.0 ml |
| --- | --- |
| Methyl paraben | 0.8 mg |
| Propyl paraben | 0.1 mg |
| Disodium Edetate | 0.1 mg |
| Sodium Metabisulfite | 2.4 mg |
| Sodium Sulfite | 0.8 mg |
| Sodium Chloride | 1.5 mg |
| Distilled water, q.s. add | 1.0 ml |

A composition prepared according to the above formulation is downwardly adjusted to a pH of 5.5 by the addition of a dilute 2.0 N solution of sulfuric acid. The resulting formulation has a shelf life of at least 36 months at 30° C.

Formulations of other aminoglycosides containing an allylic amine, as discussed above, can be similarly prepared in like manner.

We claim:

1. A pharmaceutical product comprising a sealed parenteral package, and a pH-and color-stabilized sterile aqueous antibiotic solution suitable for parenteral use consisting essentially of a parenterally acceptable salt of netilmicin, said solution having a pH in the range of 5.0–7.0, said composition being within said package.

2. A pharmaceutical product as in claim 1, wherein said sealed parenteral package is a multiple dose vial, an ampoule or a syringe.

3. A pharmaceutical product according to claim 1, wherein said salt is netilmicin sulfate in a concentration of 10–100 mg/ml of solution.

4. A pharmaceutical product according to claim 1, wherein said composition comprises an antioxidant having an equivalent $SO_2$ content not greater than 2.0 mg/ml of solution.

5. A pharmaceutical product according to claim 1 in which the pH range is 5.8 to 6.8.

6. A pharmaceutical product according to claim 5 in which the pH range is 6.2 to 6.5.

* * * * *